United States Patent [19]
DeLuke

[11] Patent Number: 5,752,523
[45] Date of Patent: May 19, 1998

[54] USE OF FACIAL GROWTH INDICATOR

[76] Inventor: Anthony G. DeLuke, 431 Riverview Dr., Youngstown, N.Y. 14174

[21] Appl. No.: 725,300

[22] Filed: Oct. 2, 1996

Related U.S. Application Data

[60] Provisional application No. 60/004,966 Oct. 10, 1995.
[51] Int. Cl.$^6$ .................................................. A61B 5/103
[52] U.S. Cl. .................................................. 128/774
[58] Field of Search .................................. 128/774, 777, 128/782; 33/511–514; 433/72

[56] References Cited

U.S. PATENT DOCUMENTS

| | | | |
|---|---|---|---|
| 4,328,620 | 5/1982 | Mack et al. | 33/174 D |
| 4,608,015 | 8/1986 | Smigel | 433/26 |
| 4,616,998 | 10/1986 | Wong | 433/73 |
| 4,843,720 | 7/1989 | Kim | 33/812 |
| 5,342,202 | 8/1994 | Deshayes | 434/270 |

OTHER PUBLICATIONS

"Biobloc Therapy", by J.R.S. Mew, printed by Flo-Print, Turnbridge Wells, U.K., 1986, pp. 118–120.

"Early Screening for Dental/Facial Growth Problems", by Anthony DeLuke, D.D.S., published in Dec. 1995 by Bidacom Associates, Inc.

"A Cephalometric Study of Mandibular Development and Its Relationship to the Mandibular and Occlusal Planes", by G.G. Bennett and J.H. Kronman, 40 Angle Orthodontics 119–128, Apr. 1970.

"Analysis—The Interim", by Robert M. Ricketts, 40 Angle Orthodontics 129–137, Apr. 1970.

"Craniofacial Width Dimensions", by Stephen H.Y. Wei, 40 Angle Orthodontics 141–147, Apr. 1970.

"Craniofacial growth in a case of congenital muscular dystrophy", by J. Kreiborg, B. Leth Jensen, E. Moller, and A. Bjork, 74 Am. J. Orthod., Aug. 1978.

"Variations in the Growth Pattern of Human Mandible: Longitudinal Radiographic Study by the Implant Method", by A. Bjork, 42 Journal of Dental Research 400–411, 1963.

"The Effect of Orthodontic Treatment on the Skeletal Pattern", by J.R.E. Mills, 5 British Journal of Orthodontics 133–143, 1978.

"A study of basal movement with rapid maxillary expansion", by Donald J. Timms, 77 American Journal of Orthodontics 500–507, 1980.

"The long face syndrome: Vertical maxillary excess", by Stephen A. Schendel, Jerome Eisenfeld, William H. Bell, Bruce Epker, and David J. Mishelevich, 70 American Journal of Orthodontics 398–408, 1976.

"Facial pattern differences in long-faced children and adults", by H.W. Fields, W.R. Proffit, W.L. Nixon, C. Phillips, and E. Stanek, 85 American Journal of Orthodontics 217–223, 1984.

"Cephalometric evaluation of patients with dentofacial disharmonies requiring surgical correction", by F.E. Khouw, W.R. Proffit, and R.P. White, 29:6 Oral Surgery, Oral Medicine, and Oral Pathology 789–798, 1970.

"Patterns of vertical growth in the face", by Surender K. Nanda, 93 Am. J. Orthod. Orthop. 103–116, 1988.

(List continued on next page.)

*Primary Examiner*—Max Hindenburg
*Attorney, Agent, or Firm*—James F. Mudd

[57] ABSTRACT

A facial growth indicator is used to measure the linear distance from an incisal edge of either a permanent or primary maxillary incisor to the intersection of a line constructed from the center of the ear, passing forward through the most anterior point on the soft tissue of the nose. A patient's measurement can be compared to a normal standard expected for a child at his or her particular age. If the child being examined has an abnormal measurement, then further diagnostic tests can be performed on the child.

4 Claims, 2 Drawing Sheets

OTHER PUBLICATIONS

"Vertical change in osseous and odontic portions of human face height between the ages of 5 and 15 years", by Bradley H. Jones, D.D.S., M.S., and Howard V. Meredith, Ph.D., 52:12 American Journal of Orthodontics, 1977. pp. 902–921.

"Inhibition or Stimulation of the Vertical Growth of the Facial Complex, Its Significance to Treatment", by Thomas D. Creekmore, D.D.S., 37 Angle Orthodontics 285–295, 1967.

"An experimental study of increased vertical dimension in the growing face" by James A. McNamara, Jr., D.D.S., Ph.D., 71:4 American Journal of Orthodontics 382–395, 1977.

"Patterns of change in mandibular and facial shape associated with the use of forces to retract the maxilla", by Sheldon Baumrind, D.D.S., M.S., and Edward L. Korn, Ph.D., 80:1 American Journal of Orthodontics 31–47, 1981.

"Growth and remodeling of the human maxilla", by Donald H. Enlow, Ph.D., and Seong Bang, D.D.S., 51:6 American Journal of Orthodontics 446–464, 1965.

"Genetic and environmental influences on morphological characteristics", 2:3 Annals of Human Biology 279–287, 1975.

"Suggestions for forecasting and monitoring facial growth", by John Mew, BDS, LDS, 104:2 American Journal of Orthodontics and Dentofacial Orthopedics 105–120, 1993.

"The Incisive Foramen—a possible reference point", by John Mew, B.D.S., L.D.S., R.C.S., 1:4 British Journal of Orthodontics 143–146.

"A radiographic and model analysis of patients manifesting partial congenital anky loglossia", by G.F. Pinsak, Masters Thesis, Farleigh Dickenson University, 1977.

"An atlas of craniofacial growth: cephalometric standards from the University School Growth Study", by M.L. Riolo, R.E. Moyers,J.A. McNamara and W.S. Hunter, Ann Arbor: Ctr for Hum. Growth, Univ. MI, 1974.

"A longitudinal cephalometric study of anterior face height in males and females 6 to 20 years of age", by S. Covo and A. Weisblatt (Thesis), Toronto, Ontario: University of Toronto, 1972.

"Progressive increase in lower face height and the use of posterior occlusal bite–block in its management", by D.G. Woodside and S. Linde–Aronson. In: Graber, L.W., ed. Orthodontics—State of the Art, essence of the science. St. Louis: CV Mosby, 1986:200–21.

"Naso–respiratory function and craniofacial growth", by S. Linder–Arouson, In: Naso–respiratory Function and Craniofacial Growth, J.A. McNamara, Jr., (Ed.), Monograph 9, Craniofacial Growth Series, Center for Human Growth and Development, The University of Michigan, Ann Arbor, 1979.

"neuromuscular and morphological adaptations in experimentally induced oral respiration", by E.P. Harold, In: naso–respiratory function and craniofacial Growth, J.A. McNamara, Jr.(Ed.), Monograph 9, Craniofacial Growth Series, Center for Human Growth and Development, The University of Michigan, Ann Arbor, 1979.

"Use of the Indicator Line to Assess Maxillary Position", Funct. Orthod. vol.:8.1.29–32 (1991).

"Measurement and the Oral Biologist", by A. Wallace Park, 40 Angle Orthodontics 138–140, Apr. 1970.

"A Concept of Facial Esthetics", by Harvey Peck, D.D.S., M.Sc.D., and Sheldon Peck, D.d.S., M.Sc.D., Angel Orthodontist, v40(4) Oct. 1970.

"ADULT-IDEAL" 18 years and older-Female 36-39mm Male 40-44mm
"FACIAL GROWTH INDICATOR"

USE OF FACIAL GROWTH INDICATOR

BACKGROUND OF THE INVENTION

This is based on provisional application Ser. No. 60/004, 966, filed on Oct. 10, 1995, the disclosure of which is incorporated herein by reference.

FIELD OF THE INVENTION

The invention provides a method of early detection and diagnosis of facial skeletal dysplasia, that is, growth problems in the bone structure of children's faces. Without some means or method of early diagnosis, a child will develop an undesired misshapen facial structure. A person with a compromised facial appearance suffers socially, psychologically and physiologically. Nasal respiratory problems are common in patients that have deficient maxillary growth. Extensive treatment is necessary to correct facial skeletal dysplasia. If the problem is detected early, the nature of the treatment is more benign and more likely to succeed.

Research studies have shown that an abnormal downward pattern of growth can be caused by nasal obstruction. Early detection would alert the pediatrician or the ear, nose and throat specialist to look for an obstruction.

PRIOR ART

Dr. John Mew discloses a facial growth indicator in his textbook, BIOBLOCK THERAPY, published in Great Britain by the author, Mew, J. R. C. and printed by Flo-Print, Tunbridge Wells, U. K. 1986, pages 118–120, the disclosure of which is incorporated herein by reference. The method in which a patient is measured with, and his application of the measurement is described. He views this measurement as useful to a clinician to access progress from adjustments made during a course of treatment.

OBJECTS OF THE INVENTION

It is an object of the invention to provide a method to differentiate between persons who have normal and abnormal dento-facial skeletal growth.

It is another object of the invention to provide a method for periodic monitoring of a child's, dento-facial skeletal growth.

Another object of the invention is to become a public health screening measure used by health care providers in their practice of testing or examination of children for healthy growth and development.

It is a further object of the invention to encourage the completion of Cephalometric radiographic analysis for those patients with probable dento-facial growth problems.

SUMMARY OF THE INVENTION

The invention provides a method to differentiate normal and abnormal dento-facial skeletal growth problems.

In accordance with the invention, a facial growth indicator is used to measure the linear distance from an incisal edge of either a permanent or primary maxillary incisor to the intersection of a line constructed from the center of the ear, passing forward through the most anterior point on the soft tissue of the nose. A patient's measurement can be compared to a normal standard expected for a child at his or her particular age. If the child being examined has an abnormal measurement, then further diagnostic tests can be performed on the child or other person. Cephalometric radiographic analysis would be the customary follow-up diagnostic procedure.

The normal measurement for children is 23 mms plus 1 mm for each year of age. A yearly 1 mm increase is observed through the completion of puberty. If a child were 7 years old, a normal measurement would be 7 plus 23 or 30 mms. If a child were 10 years of age, the normal measure would be 10 plus 23 or 33 mms. The measuring method and device can also be used for adults to estimate the extent of abnormal growth.

Abnormal measurements indicate disruption to normal growth of the upper jaw and lower jaw along with the resulting malocclusion.

In the above-identified publication, Dr. Mew describes the method in which a patient is measured with a facial growth indicator. His application of the measurement is in giving a clinician measurable treatment goals during the course of care rather than using the measurement as a screening device for the general population, as in the present invention.

Dr. Mew does not describe the need for routine early screening of children in his writings. Screening will encourage early action by parents. The first concern is to recognize the problem and weigh its seriousness accurately. Complete cephalometric analysis would be helpful to make a final determination in this regards.

Dento-facial skeletal growth guidance is a specialty area many health care providers are unfamiliar with. The parents of children six years of age and younger primarily rely on the pediatrician, family physician or general dentist for early detection of growth dysplasia. No simple screening measure currently exists. This invention provides such a technique.

DETAILED DESCRIPTION OF FIGURES

Figure 1:
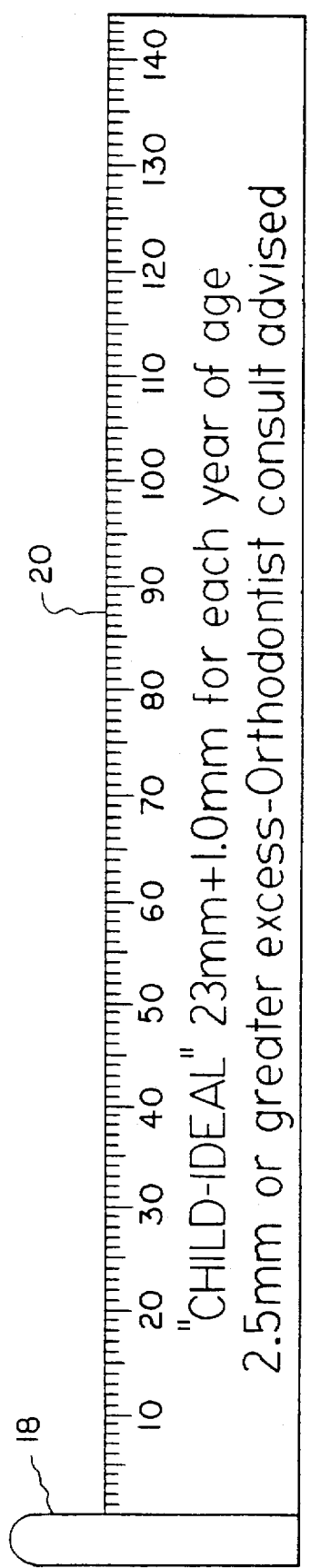
FIG. 1 shows a front view of a facial growth indicator used in the practice of the invention.

FIG. 1 shows the front face of the facial growth indicator 20 with millimetric units, numbered every 10 millimeters. The formula for 23 to 1.0 mm for each year of age is printed or etched on the metallic face of the facial growth indicator 20. A hook 18 is provided at the end of the facial growth indicator 20.

Figure 2:
FIG. 2 shows a cross sectional view of a facial growth indicator used in the practice of the invention.

FIG. 2 shows a sectional view of the facial growth indicator 20.

Figure 3:
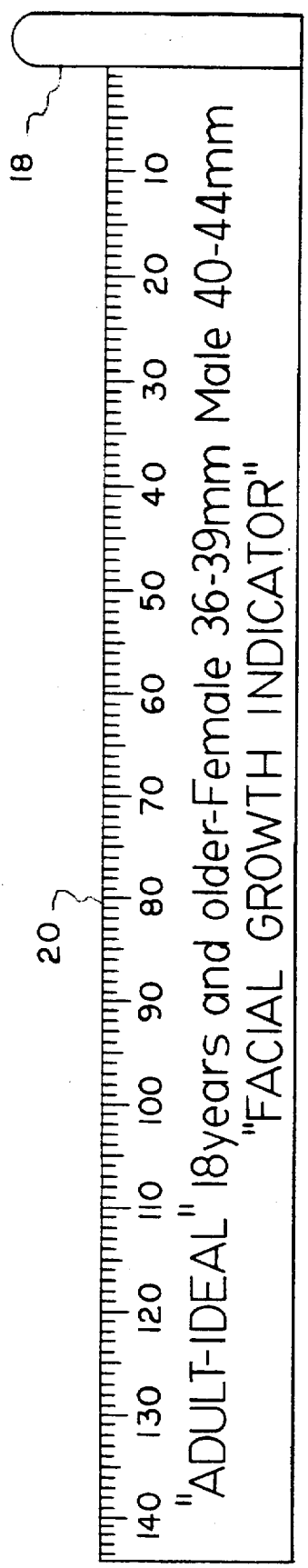
FIG. 3 shows a back view of a facial growth indicator used in the practice of the invention.

FIG. 3 shows the reverse face of the facial growth indicator 20 with a preferred formula for adults. "ADULT - IDEAL" of 18 years and older, Female 36–39 mms and Male 40–44 mms.

Figure 4C:
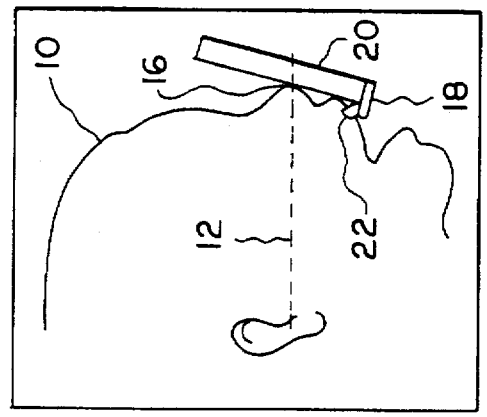
FIG. 4A, FIG. 4B and FIG. 4C illustrate the use of the facial growth indicator in making measurements on a child's face.
Figure 4B:
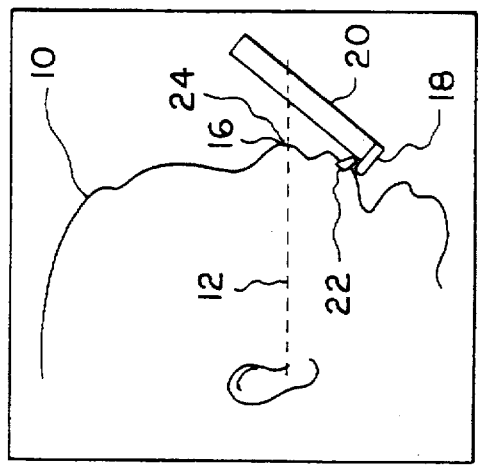
Figure 4A:
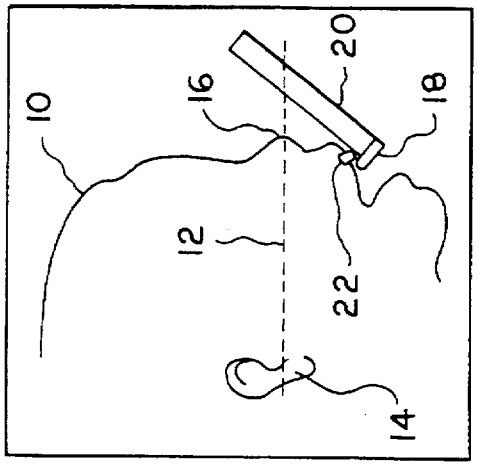

FIG. 4A shows the head of the patient 10 and illustrates how the line of sight 12 is visualized from the ear 14 of the patient to the tip of the nose 16 of the patient. The hook 18 of the facial growth indicator 20 is engaged under an upper front tooth 22 of the patient.

FIG. 4B also shows how the line of sight 12 may be marked, if desired, on the tip of the nose by a pencil mark 24 on the tip of the nose 16 of the patient.

FIG. 4C illustrates how the facial growth indicator 20 is moved to touch the tip of the nose 16 of the patient. With the facial growth indictor 20 in place, the measurement can be read from the metric index on the face of the facial growth indictor 20.

The above-identified facial growth indicators used in the invention are preferably produced from fine steel with graphics and graduations etched on the surface as shown. The hook on the end is 5/16" high and 1/4' wide and it is rounded at the top for safe usage. The facial growth indicator is fully heat and liquid sterilizable.

DETAILED DESCRIPTION OF INVENTION

Use of the Facial Growth Indicator is described as follows.

1.) Positioning of the Patient

Proper positioning of the patient is essential. When measuring a patient, the assistant must sit or stand to the side (directly lateral) of the child's head. The patient profile must be viewed. When learning to make this measurement, many persons find it helpful to place a small mark on the tip of the nose of the patient with a pencil. The patient should have relaxed facial muscles and his/her teeth should be apart only enough to place the instrument.

2.) Placement of the Facial Growth Indicator

The facial growth indicator should be rested under the edge of an upper front tooth. The tooth can be either a baby tooth or an adult tooth. It is also acceptable to measure from a partially erupted tooth. The instrument is then gradually tilted until it lightly touches the underside and front area of the nose. The nose should not be depressed by the instrument.

3) Reading the Indicator Line Measurement

The assistant must visualize a straight line from the center of the ear passing through the furthermost anterior point of the nose where a pencil mark can be made. Where this line would touch or intersect the facial growth indicator is the patient's growth indicator line measurement.

The following chart shows the normal values for children of ages 3 to 14. Higher values indicate the need for further diagnostic evaluation and/or correction.

| Age | Age plus 23 * |
| --- | --- |
| 3 | 26 |
| 4 | 27 |
| 5 | 28 |
| 6 | 29 |
| 7 | 30 |
| 8 | 31 |
| 9 | 32 |
| 10 | 33 |
| 11 | 34 |
| 12 | 35 |
| 13 | 36 |
| 14 | 37 |

* Clinical measurements in excess of these values indicate the patient is likely to be suffering facial skeletal growth dysplasia. Further diagnostic evaluation and appropriate treatment are recommended.

In a given example, a child of ten (10) years of age is examined by measuring the linear distance between the incisial edge of a permanent incisor to the intersection of the line constructed from the center of the ear passing forward through the most anterior point of soft tissue on the nose. A measured value of 38 is found and compared to the normal value of 23 mms plus 1 mm for each year of the age (equals 33.) The difference between 38 and 33 indicates that further diagnostic evaluation should be performed and treatment recommended as necessary.

In another example, a child of seven (7) years of age is examined. A measured value of 35 is obtained and compared to the normal value of 23 mms plus 1 mm for each year of age (equals 30). The difference between 35 and 30 indicates that further diagnostic evaluation should be done, and treatment is recommended as necessary.

Initial screening measurements can be taken at the age of two to three years. Screening should be completed by five years of age. If a downward pattern of growth is detected, fairly simple cures, such as clearing an airway may help the child to breathe through his/her mouth and stop the abnormal growth. If the growth dysplasia is more severe, comprehensive treatment may begin as early as five to six years of age. Without early recognition, the onset of treatment may be delayed. The majority of growth of the facial skeleton is completed by the end of the eighth year of age. After this age, it is usually too late to influence the growth of the facial skeleton, and to avoid the flatness of face and the unfortunate consequences to facial appearance which follow.

The facial growth indicator measurement is very reproducible, and always shows a downward growth of the maxilla and the mandible, which can cause the development of malocclusion and flat, unattractive faces.

It used to be thought that the nose grew independently of the rest of the face, but it is an established fact that the nose is fairly firmly anchored onto the forehead. This means the changes in the upper-lower jaw relation can be accessed by relating them to the position of the nose, so that if the face is growing downward, the distance from the nose to the upper front teeth can be measured to establish the extent of the deformity.

Like the stethoscope, thermometer, and blood pressure cuff, the facial growth indicator can be a valuable tool for the health care professional to identify those children at significant risk of facial skeletal growth dysplasia. As is the case with those instruments, a follow-up study must be completed. Traditional orthodontic cephalometric evaluation would confirm the diagnosis.

Additional information regarding this invention is disclosed in a pamphlet entitled "Early Screening for Dental/ Facial Growth Problems," published by BIDACOM Associates, Inc. December, 1995, the disclosure of which is incorporated herein, by reference.

I claim:

1. A method to differentiate between a person who has normal and a person who has abnormal dento-facial skeletal growth by measuring the linear distance from an incisal edge of either a permanent or primary maxillary incisor to the intersection of a line visually constructed from the center of the ear, passing forward through the most anterior point on the soft tissue of the nose, and comparing the measurement with normal standards for a person at his or her age.

2. A method for periodically monitoring of a person's dento-facial skeletal growth by measuring the linear distance from an incisal edge of either a permanent or primary maxillary incisor to the intersection of a line visually constructed from the center of the ear, passing forward through the most anterior point on the soft tissue of the nose, and comparing the measurement with normal standards for a person at his or her age.

3. The method of claim 2 wherein the method provides a public health screening measure for use by health care providers in their practice of examination of children for healthy growth.

4. A method to encourage the completion of Cephalometric radiographic analysis for patients with probable structural dento facial growth problems by measuring the linear distance from an incisal edge of either a permanent or primary maxillary incisor to the intersection of a line visually constructed from the center of the ear, passing forward through the most anterior point on the soft tissue of the nose, and comparing the measurement with normal standards for a person at his or her age.

* * * * *